United States Patent
Kirchhofer et al.

(10) Patent No.: US 6,193,698 B1
(45) Date of Patent: Feb. 27, 2001

(54) SYSTEM FOR LOCKING A DOSING BUTTON IN A DEVICE FOR THE ADMINSTRATION OF A PRODUCT TO BE INJECTED

(75) Inventors: Fritz Kirchhofer, Smiswald; Guido Hertig, Fraubrunnen, both of (CH)

(73) Assignee: Disetronic Licensing AG (CH)

( * ) Notice: Subject to any disclaimer, the term of this patent is extended or adjusted under 35 U.S.C. 154(b) by 0 days.

(21) Appl. No.: 09/463,015
(22) PCT Filed: Jul. 17, 1998
(86) PCT No.: PCT/CH98/00313
§ 371 Date: Mar. 31, 2000
§ 102(e) Date: Mar. 31, 2000
(87) PCT Pub. No.: WO99/03522
PCT Pub. Date: Jan. 28, 1999

(30) Foreign Application Priority Data

Jul. 18, 1997 (DE) .............................................. 197 30 999

(51) Int. Cl.⁷ ...................................................... A61M 5/00
(52) U.S. Cl. ........................... 604/211; 604/207; 604/232
(58) Field of Search .................................. 604/134–136, 604/131, 138, 181, 186, 187, 217, 218, 207, 209, 208, 232, 224, 246, 500, 506, 507, 511, 512; 222/309, 326; 128/DIG. 1, DIG. 12

(56) References Cited

FOREIGN PATENT DOCUMENTS

| 4112259 | 4/1991 | (DE) . |
|---|---|---|
| 0730876 | 9/1996 | (EP) . |
| 8808725 | 11/1988 | (WO) . |
| 9218179 | 10/1992 | (WO) . |
| 9717096 | 5/1997 | (WO) . |

*Primary Examiner*—Manwell Mendez
(74) *Attorney, Agent, or Firm*—Dorsey & Whitney LLP

(57) ABSTRACT

The present invention relates to a system for locking a dosing button in a device for the administration of a product to be injected in predetermined doses. This device comprises a body (1) with a housing (2) for the product, wherein a selected dose for injection is transported from said body out of a container (3) through a transport member (4). This device also comprises a drive member (5,7) for the transport member (4) as well as a dosing button (9) coupled to the drive member (5, 7) which is mounted so as to be capable of sliding within the body (1). The button ensures the transport of the selected dose when it is displaced from a first position into a second by actuating the drive member (5, 7). The dose is selected in the first position by rotating the dosing button (9) so that is can be moved from a first rotation position indicating that no transport is possible into a second rotation position. This device further comprises a first indicator sleeve (15) affixed to the body as well as a second indicator sleeve (17) capable of rotation together with the dosing button (9), wherein both sleeves include indication members (16, 18) for reading the selected dose according to the rotation position of said sleeves (15, 17) relative to each other. This device also comprises an anti-sliding member (11, 12, 13) which allows the dosing button to be moved from the first position into the second only when the indicator sleeves (15, 17) are placed in a zero position relative to each other thus indicating a "zero" dose. The anti-sliding member (11, 12, 13) can be unlocked by depressing on a trigger button (14), wherein the second indicator sleeve (17) releases the trigger button (14) for external access only when both indicator sleeves (15, 17) are at the zero position.

11 Claims, 5 Drawing Sheets

A-A

SYSTEM FOR LOCKING A DOSING BUTTON IN A DEVICE FOR THE ADMINSTRATION OF A PRODUCT TO BE INJECTED

This application claims the priority of PCT application PCT/CH98/00313, filed Jul. 17, 1998, and of German application 197 30 999.2, filed Jul. 18, 1997, both of which are incorporated herein by reference.

The invention relates to a system for locking a dosing button in an apparatus for metered administration of an injectable product as it reads from the preamble of claim 1.

Apparatuses for metered administration of an injectable product are known, in particular, in insulin treatment, these being, for example, so-called injection pens, with which a diabetic is able to inject himself with the desired dose of insulin. Such injection pens comprise a so-called dosing button protruding like the push-button of a ballpoint pen from an opening in the housing of the injection pen. To prepare the injection, the dose to be injected is selected or set by rotating the dosing button relative to the housing. By rotation of the dosing button, a drive member is preset. To make the injection, the dosing button is then pressed from a first end position a little further in the housing up to a second end position, and thereby actuates the preset drive member. The latter in turn acts in the preset manner on a pumping member, generally a piston, which is shiftably accommodated in an ampoule filled with insulin, and which, due to the effect of the drive member, displaces the preset insulin dose from the ampoule through an injection needle. At the end of injection, the dosing button is latched in its second end position, from which it only moves itself back into its first end position immediately prior to the next injection, in which a renewed dose is again possible. In such an apparatus as known, for example, from EP 0 730 876 A2 and DE 41 12 259 A1, shifting the dosing button from its latched second end position into the first end position is only possible when an indicator member indicates the zero position of the dosing button. The starting position of the dosing button prior to metering the amount of product to be administered by the next injection is defined and coordinated with the indicator. The design for achieving this is, however, highly complicated. It is the object of the invention to assure by as simple means as possible that an indicated rotation position of a dosing button of a device for metered administration of an injectable product coincides with the actual rotation position of the dosing button during metering.

This object is achieved by the subject matter as it reads from claim 1.

A device for metered administration of an injectable product comprises a housing, including an accommodation for the product. For an injection, a selectable dose of the product held in a container is pumped from the container by means of a pumping member. The container may be formed directly by the housing, i.e., by the accommodation thereof. Preferably serving as the container is an ampoule, accommodated in the accommodation of the housing, the accommodation being configured as an ampoule compartment. The pumping member is preferably formed by a piston, shiftably accommodated in the container. The pumping member may also be formed, however, by a squeezing mechanism with which a pliant tube is squeezed between two squeeze positions, i.e. a peristaltic pump. In principle, metering rotary pumps may also be put to use. The injectable product is primarily a liquid solution of an active substance, for example, insulin or other liquid medicaments.

When use is made of a piston, the drive member for the pumping member is preferably formed by a piston rod which moves against the piston, pressing the piston in the direction of a container outlet port so that the product is displaced from the container.

Coupled to the drive member is a dosing button, shiftably mounted in the housing, which in being shifted from a first shift position into a second shift position actuates the drive member such that the selected dose of the product is pumped by the pumping member. In the first position of the dosing button, the dose is selected on rotation of the dosing button from a first rotation position for zero delivery into a second rotation position assigned to the selected dose. The coupling is preferably mechanical, but, in principle, may be any other type of coupling, for instance an electrical or electromechanical coupling.

For indicating the rotation position of the dosing button and thus the dose of the product selected thereby, a first indicator sleeve, affixed to the housing, and a second indicator sleeve, rotatable with the dosing button, are provided. The indicator sleeves are provided with indicator members, permitting reading of the selected dose based on the rotation position of the indicator sleeves relative to each other. Preferably, one of the indicator sleeves surrounds the other. In this arrangement, dose values or symbols representing dose values are marked on a scale of the inner indicator sleeve which are readable through a window in the outer indicator sleeve. The indicator sleeves could, however, also be arranged in sequence along a common longitudinal axis, the relative rotation position then being indicated, for example, by means of a marking on the shell surface of the one indicator sleeve, opposite a corresponding scale on the other indicator sleeve. Preferably, the inner indicator sleeve is arranged affixed to the housing or is itself formed by part of the housing, and the outer indicator sleeve is rotated by turning the dosing button around the inner indicator sleeve. In principle, it is also possible in this shell-like arrangement of the indicator sleeves that the inner sleeve is rotatable with the dosing button and the outer sleeve is affixed to the housing.

To ensure a defined starting condition of the apparatus prior to an injection, a system for locking the dosing button is provided in the form of an anti-shifting member. This system for locking the dosing button prevents an uncontrolled, i.e. accidental, shifting of the dosing button from the second position back into the first position. The dosing button can only move back into its first position when the indicator sleeves are located in the zero position relative to each other in which the dose "zero" is indicated. In the locked second position, the dosing button is preferably locked not only from shifting out of place, but also from rotating out of place relative to the housing. The system for locking the dosing button may be configured as an anti-shifting member and simultaneously as an anti-rotation lock. An anti-rotation lock may also be provided elsewhere. In principle, it is likewise conceivable, however, that the dosing button rotates idly in its proximal second position by it being uncoupled from this position by the drive member.

In accordance with the invention, the system for locking the dosing button is released by simply pressing a trigger button which, however, for external access, namely finger pressure, is only released from the second indicator sleeve, rotatable with the dosing button, in the zero position of the first and second indicator sleeve.

This arrangement for unlocking the system locking the dosing button in accordance with the invention is easy to build and compact, and is particularly robust and operationally reliable, not least by using a sleeve to shield and release the trigger button. This sleeve can rotate simultaneously with the dosing button in the distal first dosing button position, releasing of the trigger button occurring dependent on the rotation position of this sleeve.

In accordance with the invention, the second indicator sleeve comprises a breakthrough, which, in the zero position of the first and second indicator sleeve, is located above the trigger button so that the trigger button is exposed for being pressed. However, as long as the second indicator sleeve is not positioned in the zero position of the first indicator sleeve, it covers the dosing button to shield it from external access, thereby preventing unlocking of the anti-shifting member. In a first example embodiment, the breakthrough is a simple open breakthrough, sufficiently large so that the user has finger access through it. In a second example embodiment, the breakthrough at the second indicator sleeve creates a pressing aid, preferably in the form of a tab which can be pressed radially inwards and springs back elastically upon removal of the actuating force.

The invention is preferably utilized in injection apparatuses, in particular, in the configuration form of a pen; it being likewise usable in infusion/injection apparatuses.

Preferred example embodiments of the invention will now be detailed with reference to the Figures in which.

Figure 1:
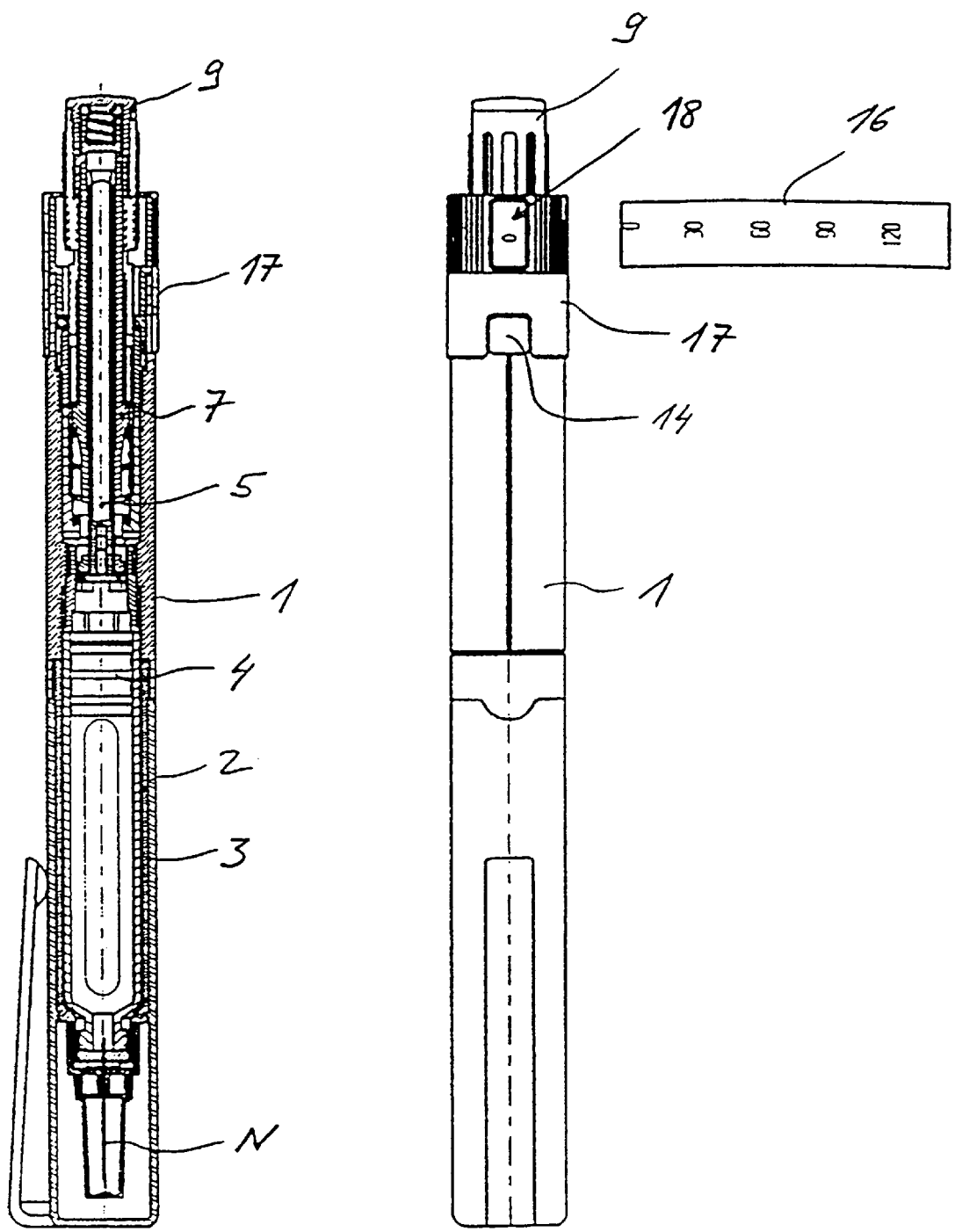
FIG. 1 is an illustration of an injection pen including a system for locking the dosing button, means for releasing the lock and dose indication members being configured in accordance with a first example embodiment.

Referring now to FIG. 1, illustrated is an injection apparatus in the form of a so-called injection pen. Injection pens serve primarily for multiple, self injection of a liquid active substance solution in dosed amounts, for example, insulin or hormone preparations.

The injection apparatus comprises an elongated housing, including a proximal housing part, serving as an accommodation 2 for accommodating the active substance solution to be administered, and a distal housing part 1. Accommodated in housing part 1 is a drive for driving a pumping member, this being a piston 4 in the present example embodiment. Accommodated in the accommodation 2 is an ampoule 3 filled with the active substance solution. The active substance solution is displaced by the advance movement of the piston 4 in the direction of the ampoule outlet via an injection needle N, adjoining the ampoule outlet.

Figure 2:
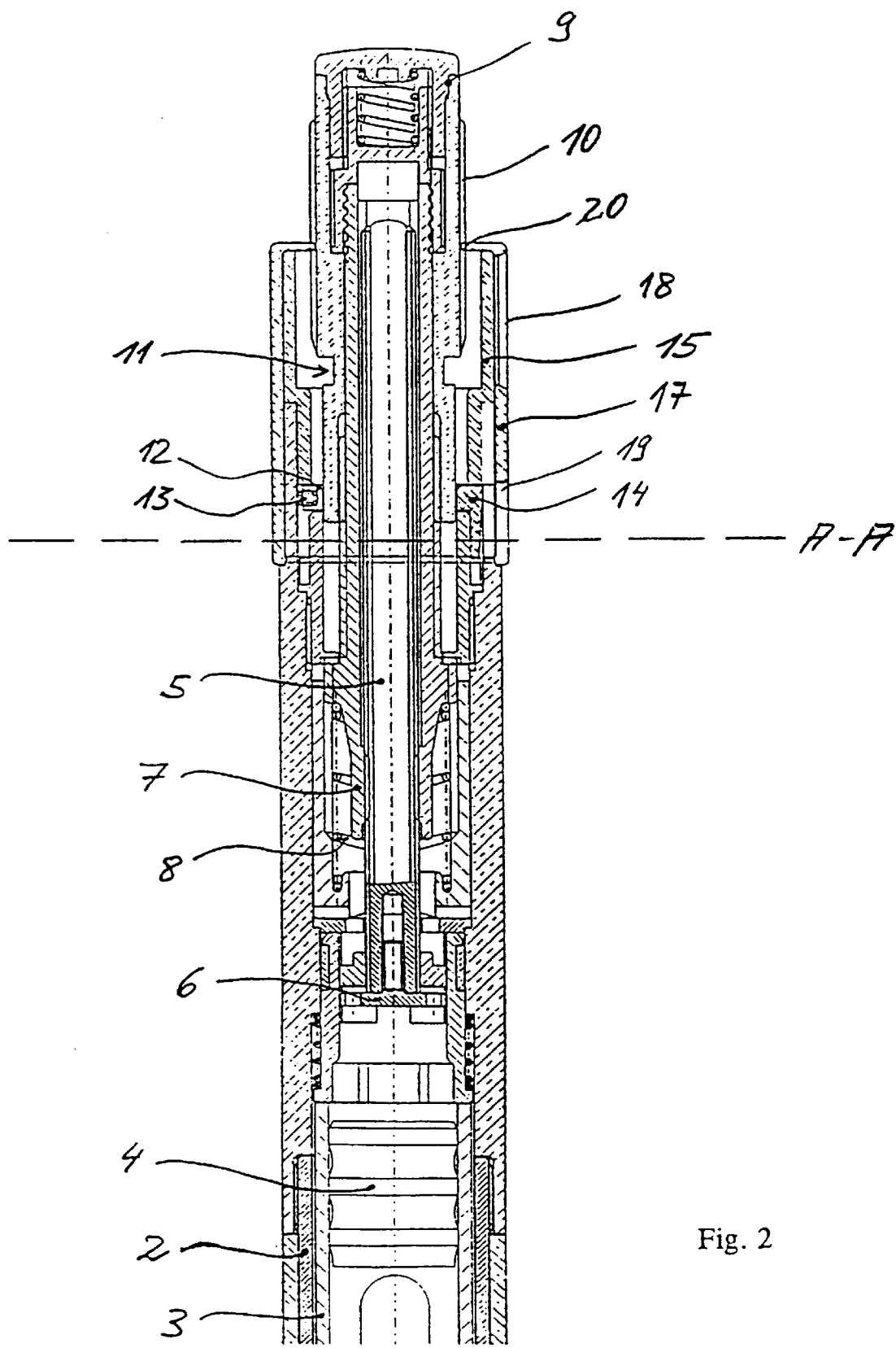
FIG. 2 is a longitudinal section in accordance with FIG. 1.

The advance movement of the piston 4 is caused by the contact pressure of a threaded rod 5. The threaded rod 5 forms the driven member of a spindle drive, which, in the example embodiment, is configured single-stage with the threaded rod 5 and a threaded sleeve 7, surrounding the latter as the drive member. To advance the piston 4, the threaded sleeve 7 together with the threaded rod 5 is advanced against an elastic return force by actuation of a dosing button 9 in turn in the piston advance direction towards the distal end of the piston. The dosing button 9, the drive members 5, 7 and the piston 4 are linearly shifted along a common axis, indicated dot-dashed in FIG. 1, the shifting axis. In this arrangement, the distance by which the dosing button 9 and the drive members 5, 7 are shifted on actuation or injection is always the same. The advance movement occurs from a distal first position, as shown in FIGS. 1 and 2, into a proximal second position, assumed by the dosing button 9 and, in the example embodiment, with it also the drive members 5, 7, once injection has taken place. In this arrangement, the distance covered by the piston 4, as influenced by the drive 5, 7, and thus the active substance dose administered per injection is variable.

The dose selected by means of the dosing button 9 is indicated in a window 18 of an indicator sleeve 17. The doses, which can be adjusted continuously, or discretely as in the example embodiment, are marked on a ring scale 16 affixed to the housing, this ring scale being concentrically surrounded by the indicator sleeve 17 in the region of its window 18. A sleeve component, arranged affixed to the housing and mounting the ring scale, is described hereinafter as the first indicator sleeve, and the indicator sleeve 17, rotatable with the dosing button 9, is described the second indicator sleeve. In accordance with the invention, the second indicator sleeve 17, rotatable with the dosing button 9, cooperates with a trigger button 14 such that the rotation position of the dosing button 9 in the distal first position of the dosing button 9, as illustrated, always correlates to the dose readable in the window 18 defined.

Referring now to FIG. 2, there is illustrated on a magnified scale the distal part of the longitudinal section as shown in FIG. 1. The dosing button 9 is located, with respect to its shifting path, in its distal first position as shown in FIG. 1. In the first position, the dose of active substance to be administered by the next injection is pre-selected by rotating the dosing button 9 around its longitudinal axis, i.e. dosing takes place.

At its distal end, the dosing button 9 comprises a sleeve part, closed off by an exchange part. The sleeve part of the dosing button 9 protrudes through a distal face of the housing 1. In the region of the sleeve part, the dosing button 9 is connected to the threaded sleeve 7 by an anti-rotation lock. Thus, rotating the dosing button automatically slaves in rotation the threaded sleeve 7 around its longitudinal axis. The threaded rod 5 is linearly guided secured against rotation so that a rotation of the threaded sleeve 7 automatically results in a linear shift of the threaded rod 5. At its proximal end facing the piston 4, the threaded rod 5 comprises a flange or plunger 6, with which it advances the piston 4 in the ampoule 3 on actuation of the dosing button, i.e. on it being displaced from the represented distal first position into a proximal second position pressing against the piston 4. Metering is done in the way just described by setting the clearance between the proximal face of the threaded rod plunger 6 and the backward face of the piston 4 in the distal first position of the dosing button 9. The shifting path of the threaded rod plunger 6 is the same in length for each injection. Advancement is made against the elastic restoring force of a compression spring 8, disposed between an appendage of the housing 1 and a corresponding companion appendage on the threaded sleeve 7. The compression spring 8 attempts to push back to its distal first position the complete actuating means, essentially consisting of the threaded sleeve 7, threaded rod 5 and dosing button 9.

An anti-shifting member is provided to prevent uncontrolled injections, which could otherwise not be ruled out, if, after each injection, the actuating means itself springs back into its starting position, i.e. into its distal first position. The anti-shifting member comprises a ring, clasping around the sleeve part of the dosing button 9 and including a cam 12, engaging in a recess 11 in an outer shell surface of the sleeve part of the dosing button 9, when the dosing button 9 is located in its proximal second position. In this example embodiment, the recess 11 is configured as a ring groove extending all around the circumference.

So that the cam 12 snaps into place in the recess 11, when the dosing button 9 is located in its proximal second position, the cam 12 is pre-stressed radially on the outer shell surface of the sleeve part of the dosing button 9 by a compression spring 13, arranged between the housing part 1 and the rear side of the cam. The ring with the cam 12 comprises a trigger button 14, diametrical opposing the cam 12. When the cam 12 is pushed into the recess 11 in the proximal second position of the dosing button 9, the trigger button 14 is urged outwardly into, or even through, a corresponding breakthrough of the housing 1. Conversely, in the second position of the dosing button 9, locked in place by the cam 12, the cam 12 is moved out of the recess 11 against the elastic restoring force of the compression spring 13 by the manual pressure exercised on the trigger button 14, and the anti-shifting member is thereby released. The, thus, unlocked dosing button 9 is returned to its distal first position by the elastic restoring force of the compression spring 8 together with the threaded sleeve 7 and the threaded rod 5.

In the distal first position of the dosing button 9, the second indicator sleeve 17 is rotated with the dosing button 9, to which it is positively connected. In the example embodiment, it slaves the dosing button in rotation on a ratio of 1 to 1; although, in principle, any increase or reduction of the rotary movement of the dosing button 9 to the second indicator sleeve 17 is conceivable. This form fit anti-rotation lock is achieved by the dosing button 9 meshing tooth-like with the second indicator sleeve 17. For this purpose, the cylindrical—in the example embodiment circular cylindrical—sleeve part of the dosing button 9 comprises axially extending ridges and furrows 10 arranged uniformly distributed about the circumference of an outer shell surface corresponding to the scale divisions, which engage with the companion ridges and furrows 20 on an inner shell surface of the second indicator sleeve 17, preventing the second indicator sleeve 17 from being rotated relative to the dosing button 9.

The second indicator sleeve 17 surrounds the first indicator sleeve 15, the latter in turn surrounding the dosing button 9. In the example embodiment, the sleeve part of the dosing button 9 and the two indicator sleeves 15 and 17 are arranged concentrically, although it would be just as possible to arrange the indicator sleeve, rotating with the dosing button 9, within the indicator sleeve affixed to the housing or even to arrange the two indicator sleeves in sequence in a modification of the example embodiment.

The second indicator sleeve 17 is locked in place axially at the housing 1 and mounted to rotate around its longitudinal axis. In the example embodiment, the shifting axis of the dosing button, as well as that of the actuating means 5, 7, 9 and the axis of rotation of the second indicator sleeve 17 coincide.

Figure 3:
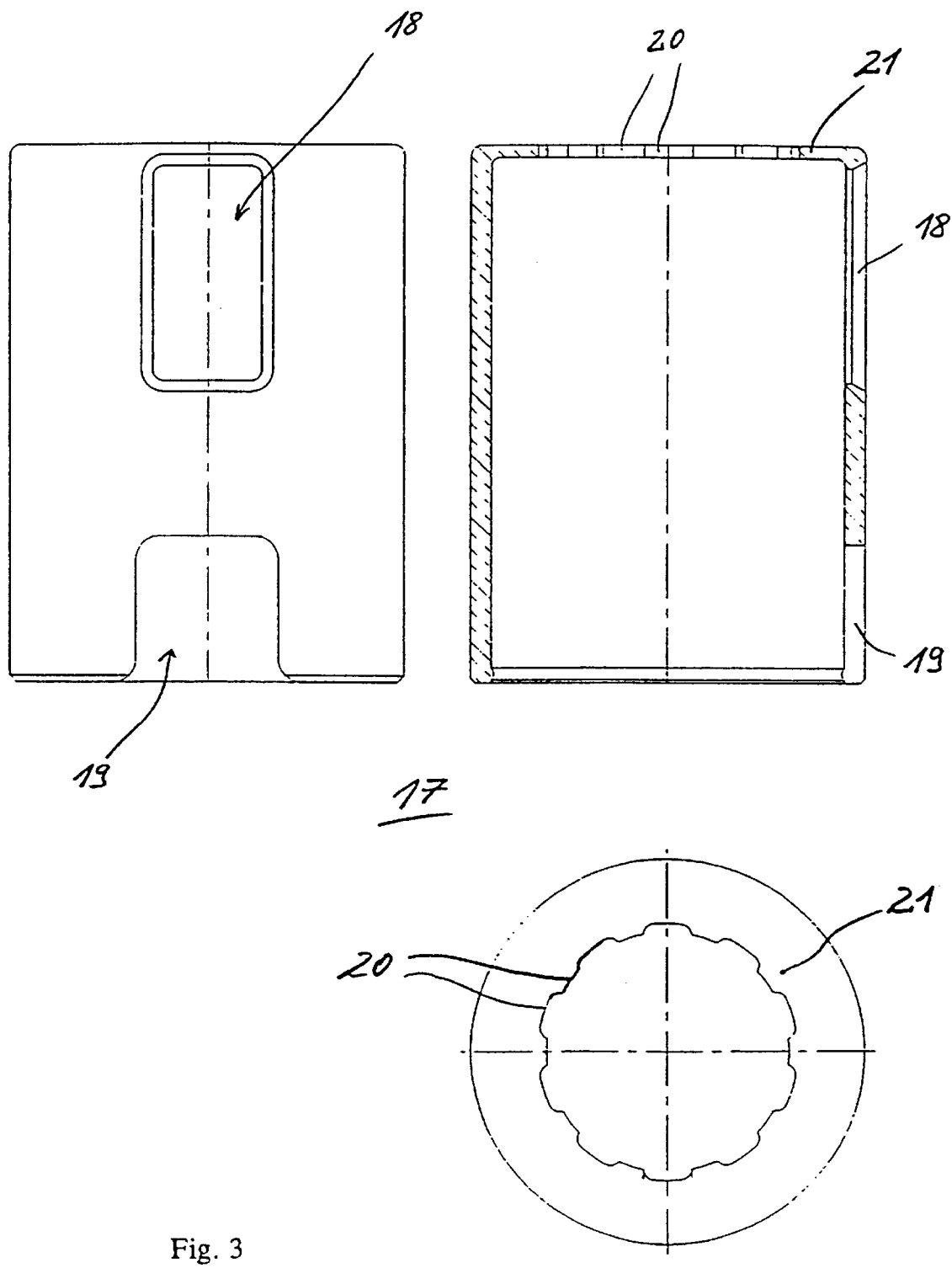
FIG. 3 is an illustration of an indicator sleeve according to FIGS. 1 and 2.

Referring now to FIG. 3, there is illustrated the second indicator sleeve 17 in one view, in a longitudinal section and in a plan view of the distal face with the tooth-like ridges and furrows 20. The second indicator sleeve 17, with the exception of its indicator window 18 and a breakthrough 19, is configured as a closed envelope. In the example embodiment, it is simply circular cylindrical with a shoulder protruding radially inwards and extending all around the circumference. The ridges and furrows 20 are configured circumferential at an inner circumferential edge of the shoulder, it being by this shoulder that the second indicator sleeve 17 juts out of the facing distal circumferential edge of the housing 1, formed in this distal portion by the first indicator sleeve 15 (FIG. 2). In its distal shell portion, in which the window 18 is located, the second indicator sleeve 17 is roughened for a better grip. In its proximal shell portion, it comprises the breakthrough 19, the dimensions of which are selected so that the trigger button 14 protrudes through this breakthrough 19 for actuation by the user of the injection apparatus, i.e. permitting squeezing towards the shifting axis. To minimize its surface area, the breakthrough 19 is configured as a recess opening towards the proximal circumferential edge of the second indicator sleeve 17 for edgewise tactile engagement by the user. The indicator window 18 and the breakthrough 19 are arranged juxtaposed in the longitudinal direction of the second indicator sleeve 17, so that the trigger button 14 is visible to the user, or the breakthrough 19 coincides with the trigger button 14, when the indicator window 18 indicates zero dosing.

Positive locking between the second indicator sleeve 17 and the dosing button 9 exists merely as regards the rotary movement, i.e. without obstructing shifting of the dosing button 9 relative to the second indicator sleeve 17. The ridges and furrows 10 at the dosing button 9 extend over the dosing button 9 or the sleeve part thereof also only as far as the distal end of the dosing button 9 so as to prevent positive engagement of the second indicator sleeve 17 in the proximal second position of the dosing button 9. In the second dosing button position, the second indicator sleeve 17 is free to rotate about its axis of rotation.

Freedom of rotation of the indicator sleeve 17 is restricted merely with respect to the first indicator sleeve 15 or the housing 1 in that the second indicator sleeve 17 is used to limit the maximum dose selectable with the dosing button 9. In the example embodiment, the dosing button 9 can be rotated by a maximum 360E or almost 360E. This is achieved, as evident from FIG. 4 from both views of the cross-section taken along the line A—A in accordance with FIG. 2, in that the second indicator sleeve 17 is guided in a direction of rotation in which the dose values indicated in the window 18 increase, against a stop affixed to the housing. A rotation of the dosing button 9 in the other direction of rotation, i.e. in the direction of reducing dose values, is already prevented by known latching means, for example a ratchet, acting between the dosing button 9 or the drive sleeve 7 and the housing 1. The direction of rotation of the second indicator sleeve 17 and the dosing button 9 upon metering is indicated by arrow D in the two section views in FIG. 4.

The stop for the rotary movement of the second indicator sleeve 17 is formed by a notch 22 and a spring tongue 23 engaging the notch 22 by a latching nose or cam. The notch 22 extends axially over an inner shell surface area of the second indicator sleeve 17. The spring tongue 23 is formed between two slots extending circumferentially at the housing 1 with a short axial slot connecting these two slots, i.e. the housing is slotted un-shaped in the region of its shell surface area enveloped by the second indicator sleeve 17. The latching nose or cam protrudes radially outwards from the springy end of the tongue 23 level with the notch 22.

When the second indicator sleeve 17 is turned in the direction of the arrow D in the course of a metered administration, the second indicator sleeve 17 may be rotated, and via the mechanical coupling, the dosing button 9, maximally until coming up against a stop surface area of the notch 22, said stop surface area being a rear stop surface area with reference to the direction of rotation D. The upper view of FIG. 4 shows the second indicator sleeve 17 shortly after commencement of a metered administration, the lower view being shortly before the end of selection of the maximum dose.

In the stop being formed the notch 22 is caused to snap radially outwards to one side from the inner shell surface of the second indicator sleeve 17, while the notch 22 on the opposite side runs skew to the radials so that the second indicator sleeve 17 can be rotated past this skew limiting surface area of the notch 22 opposite the housing 1. In this direction of rotation, i.e. contrary to the indicated direction of rotation D, the second indicator sleeve 17 is rotated back into its zero position after the injection. The effect of cooperation of the notch 22 with the springy tongue 23 goes beyond a pure stopping function so that the second indicator sleeve 17 is arrested in its zero position, in the sense that the user is aware, at least by tactile indication, of having rotated the second indicator sleeve 17 into its zero position prior to the next injection. At the same time, handling of the injection pen is facilitated since the second indicator sleeve 17 is maintained in its zero position and prevented from by automatically rotating when the trigger button 14 is pressed.

Figure 4:
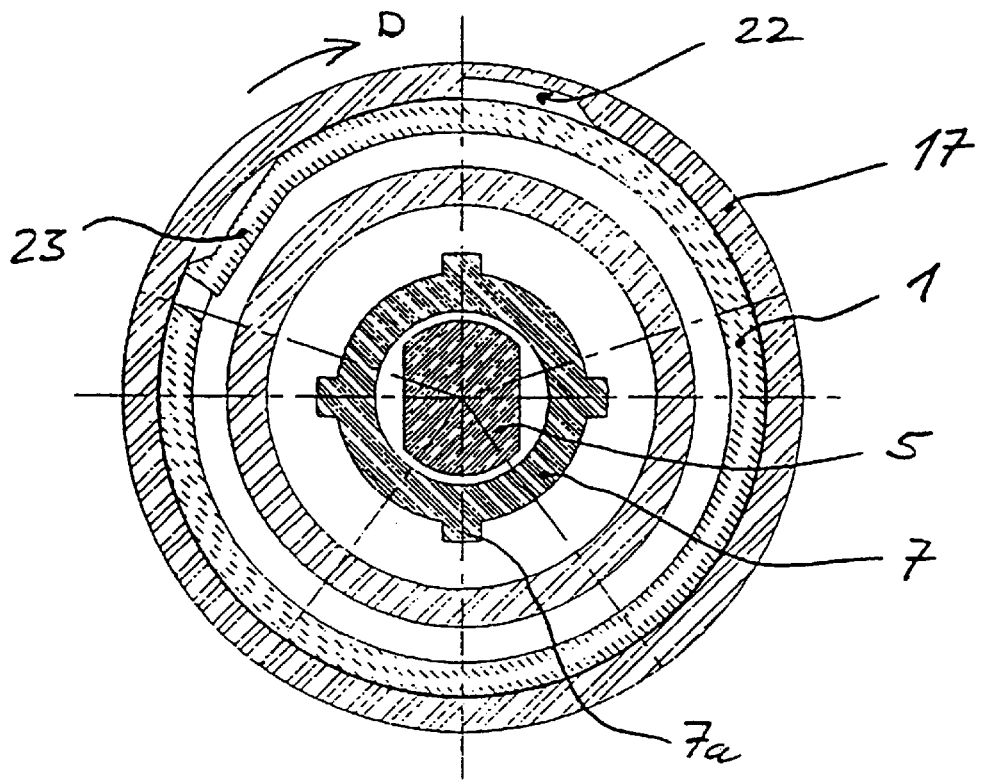
FIG. 4 is a cross-section taken along the line A—A in accordance with FIG. 2.
Figure 4:
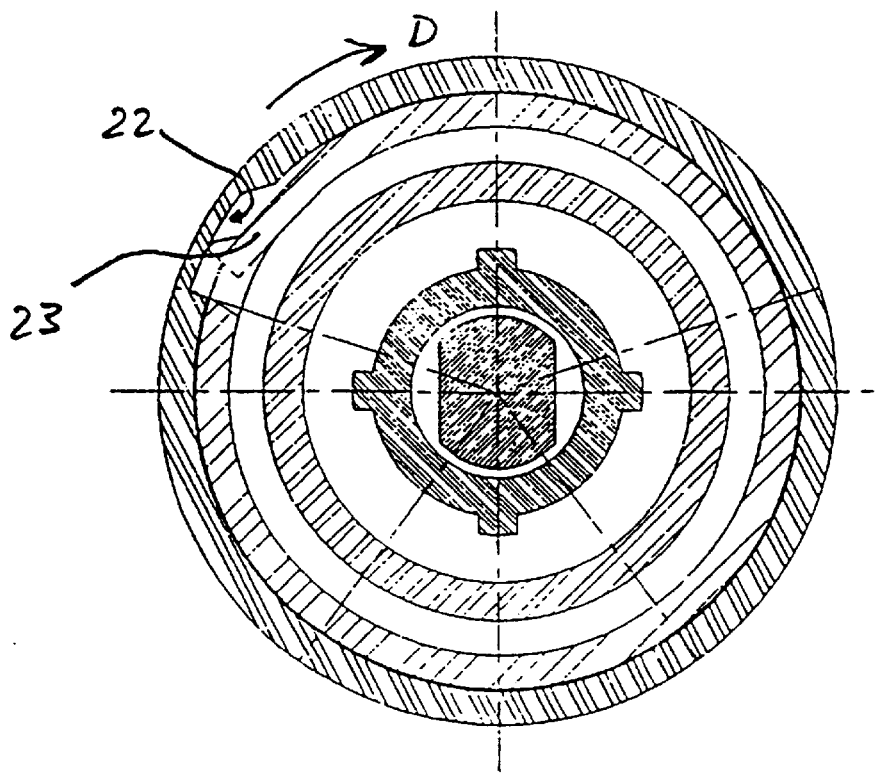

Also shown in FIG. 4 is the anti-rotation lock of the threaded rod 5 relative to the housing 1, namely the two flats opposite each other. Also represented is the anti-rotation lock of the threaded sleeve 7 in the form of guides 7a, protruding radially outwards, which are linearly guided in corresponding recesses in the side of the housing immediately after pressing of the dosing button 9.

When the dosing button 9, and thus in the example embodiment, the complete actuating means 5, 7, 9 for injecting the selected dose is moved into the second position, then the sleeve part of the dosing button 9 slides along the cam 12. In this arrangement, the trigger button 14 is located in an inner position as viewed radially to the shifting axis. Once the dosing button 9 has reached its second position, the recess 11 is level with the cam 12. Due to the force of the compression spring 13, the cam 12 snaps into place in the recess 11 on the dosing button 9. Since the cam 12 and the trigger button 14 are rigidly connected to each other via a ring, the snap-in action of the cam 12 causes the trigger button 14 to shift radially away from the shifting axis outwardly through a corresponding opening in the housing 1. The second indicator sleeve 17 thus extends, starting from its distal face, so far over the first indicator sleeve 15 or housing 1 that it still covers the trigger button 14 and, in this way, shields against external access. The trigger button 14 does not project radially out over the housing 1 or first indicator sleeve 15 or only so far radially that it does not hinder the rotary movement of the second indicator sleeve 17. It is only in the zero position of the second indicator sleeve 17, in which its indicator window 18 windows the dose value of the ring scale 16 corresponding to the zero delivery, that it releases access to the trigger button 14.

In this position of the second indicator sleeve 17, pressing the trigger button 14 urges the cam 12 out of the recess 11 against the force of the compression spring 13, and the actuating means 5, 7, 9, in particular, the dosing button 9, is shifted by the compression spring 8 into the distal first position of the dosing button 9. As soon as the return shifting movement starts, the ridges and furrows 10 and 20 of the dosing button 9 and of the second indicator sleeve 17 positively engage, it being at this moment that the dosing button 9 and the second indicator sleeve 17 are immediately again anti-rotation locked relative to each other. Any minor rotation of the second indicator sleeve 17 at the moment the ridges and furrows 10 and 20 mutually engage is, in any case, so slight that the fixed assignment of the dosing button rotation position and the indication remains assured.

Figure 5:
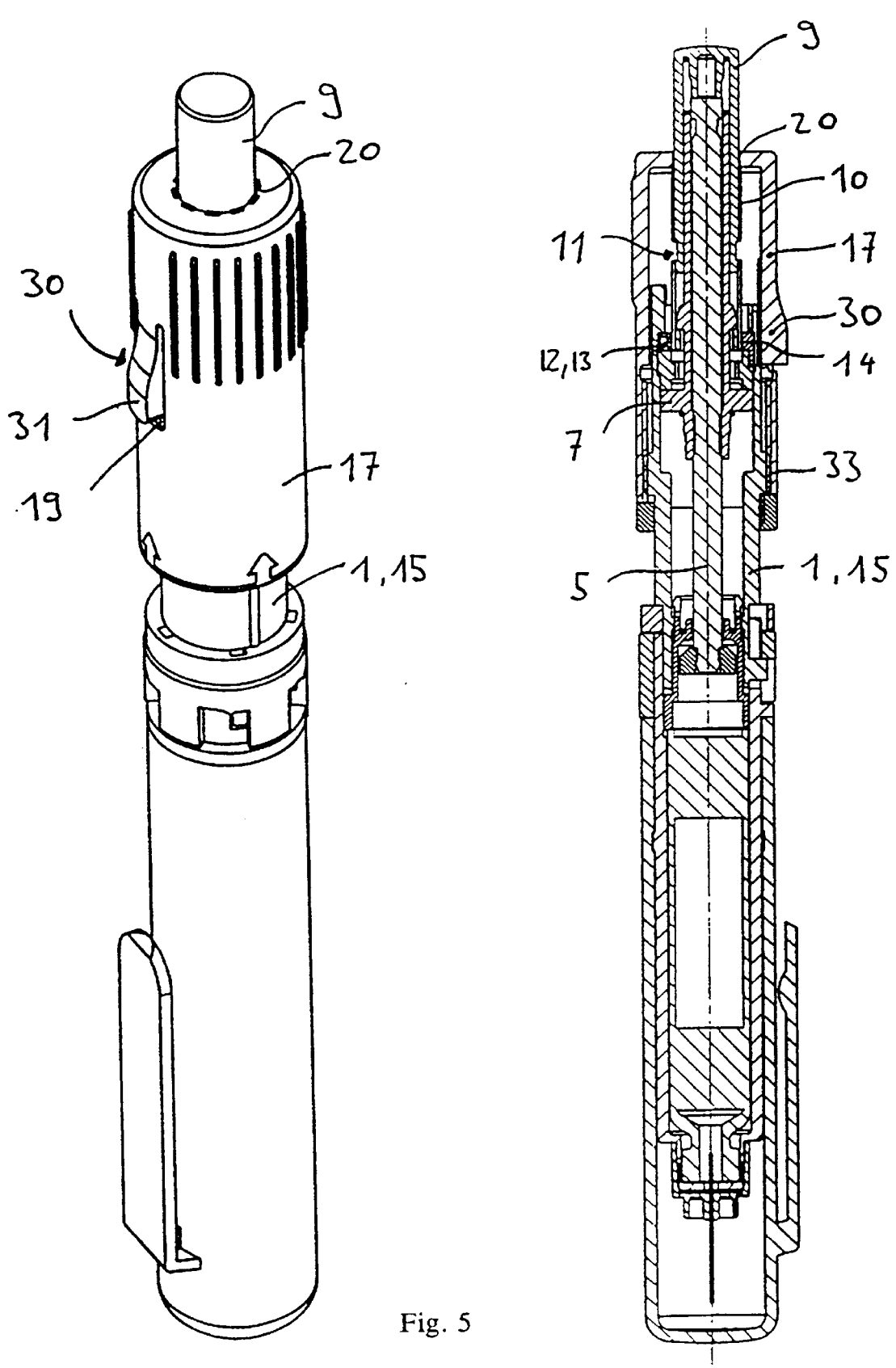
FIG. 5 is an illustration of an injection pen comprising a system for locking a dosing button, means for releasing the lock and dose indication members being configured in accordance with a second example embodiment.

Referring now to FIG. 5 there is illustrated, in a view and in a longitudinal section, an injection pen comprising an alternative configuration of the second indicator sleeve 17 for releasing the system for locking the dosing button. Furthermore, the scale for indicating the set dose is not applied simply ring-shaped to the first indicator sleeve 15, but in the form of a helix with the scale values applied in sequence in the direction of advancement and extending around the circumference of the shell surface of the second indicator sleeve. The scale markings for the dosing units may be represented magnified, as compared to those shown in the example embodiment evident from FIGS. 1 to 4, to thus facilitate easier and more reliable reading. Accordingly, the second indicator sleeve 17 is also not fixed in its axial position at the housing, it instead, upon metered administration and the rotary movement of the dosing button 9 associated therewith, being shifted proximally on the housing 1 so that a window 31 of the second indicator sleeve 17 windows the scale during metered administration to read off the scale. Incidentally, the pen as shown in FIG. 5 may be viewed as being the same as the pen of FIGS. 1 to 4, i.e. any further differences in design being irrelevant as regards the invention. Accordingly, components like in function with those as used in FIGS. 1 to 4 are identified by the same reference numerals, and reference is made to the corresponding description relating to FIGS. 1 to 4.

In this example embodiment, restricting the rotation of the second indicator sleeve 17 relative to the first indicator sleeve 15 is preferably eliminated.

In the pen as shown in FIG. 5, the first indicator sleeve 15 simultaneously forms the distal housing part 1 accommodating the drive.

To set the dose to be administered, the dosing button 9 is rotated around its longitudinal axis. Due to the anti-rotation lock, again configured at 10 and 20, the second indicator sleeve 17 is compulsory slaved in the rotation. It is compulsory connection between dosing button 9 and second indicator sleeve 17 that leaves it the user the choice of turning the second indicator sleeve 17 or the dosing button 9 for setting the dose. The second indicator sleeve 17 is connected to the distal housing part 1 by means of a thread 33, this connection causing a compulsory forward shifting of the second indicator sleeve 17, when the dosing button 9 is rotated in its first position.

The dose setting "0" is provided directly to the trigger button 14, which, otherwise, is configured the same as the cam 12 and the spring 13 of the example embodiment of FIGS. 1 to 4, and cooperates with the annular groove 11 of the dosing button 9. The breakthrough 19 and the indicator window coincide in the second indicator sleeve 17 of the example embodiment as shown in FIG. 5, i.e. the dose values of the scale are read in the region of the breakthrough 19, which, at the same time, again forms means for releasing the system for locking the dosing button. For this purpose, the breakthrough 19 is configured in the form of a u-shaped slot. Protruding into the breakthrough 19, is a tab 30, which may be formed quite simply by the configuration of the u-shaped slot in the second indicator sleeve 17 or, as in the example embodiment, by a tab jutting out from the outer shell surface. The tab 30 may thus be urged radially inwards particularly easily, when released it snaps back into its starting position due to its elasticity.

One portion of the elastic tab 30, the proximal portion in the example embodiment, is configured as a window 31. To enable better and more reliable reading of the scale of the first indicator sleeve 15, the window 31 acts as a magnifying means or magnifying glass.

When the dosing button is in its proximal second position, in which it is maintained by the cam 12, positively locking in the groove 11, the second indicator sleeve 17 is rotated back, thereby following the scale and the thread 33 and thereby simultaneously shifted distally, until the trigger button 14, having the "0" marking, is covered by the window 31 of the tab 30. In this position, the trigger button 14 is shifted transversely by pressing in the tab 30, as already explained with reference to FIGS. 1 to 4, so that the cam 12 is urged out of the groove 11, and the dosing button 9, with the drive 5, 7, returns to the first position.

In a further modification of the means for releasing the system for locking the dosing button, a kind of tab may also be formed by a transparent, elastic half-dish, which covers the breakthrough—again of the surface type—and thereby preferably forms a pressing aid, jutting out from the outer shell surface of the second indicator sleeve. Likewise, a pressing aid, comparable to the tab 30, could also be used in conjunction with the second indicator sleeve 17 of the example embodiment of FIGS. 1 to 4.

What is claimed is:

1. A system for locking a dosing button in a device for metered administration of an injectable product, the apparatus comprising
   a) a housing, including an accommodation for said product, of which a selected dose for an injection is delivered from a container by means of a pumping member,
   b) a drive member for said pumping member,
   c) a dosing button coupled to said drive member, shiftably mounted in said housing, said dosing button, when shifted from a first position into a second position by actuation of said drive member, resulting in said selected dose being delivered, this dose being selected in said first position by rotation of said dosing button from a first rotation position for zero delivery into a second rotation position,
   d) a first indicator sleeve, affixed to said housing, and a second indicator sleeve, rotatable with said dosing button, said indicator sleeves comprising indicator members, permitting reading off said selected dose due to the rotation position of said indicator sleeves relative to each other, and
   e) an anti-shifting member, permitting shifting of said dosing button from said second position back into said first position only when said indicator sleeves are located in a zero position relative to each other indicating a "zero" dose, characterized in that
   f) said anti-shifting member is released by pressing a trigger button, and
   g) said second indicator sleeve releases said trigger button for external access only in said zero position of said indicator sleeves.

2. The system for locking a dosing button according to claim 1, wherein said second indicator sleeve comprises a breakthrough which is located radially above said trigger button in said zero position of said indicator sleeves.

3. The system for locking a dosing button according to claim 2, wherein said breakthrough is formed by a recess open at a face circumferential edge of said second indicator sleeve.

4. The system for locking a dosing button according to claim 2 wherein, by means of said breakthrough at said second indicator sleeve, an elastic pressing aid is formed which, in said zero position of said indicator sleeves, protrudes radially above said trigger button and is pressable against said trigger button.

5. The system for locking a dosing button according to claim 3 wherein said second indicator sleeve is rotatively mounted around a shifting axis of said dosing button in surrounding said dosing button at said housing.

6. The system for locking a dosing button according to claim 1 wherein said second indicator sleeve surrounds said first indicator sleeve and said selected dose is readable through a window of said second indicator sleeve from a scale on said first indicator sleeve.

7. The system for locking a dosing button a according to claim 1 wherein said dosing button and said second indicator sleeve are connected to each other in said first position of said dosing button by means of an anti-rotation lock, said anti-rotation lock being preferably a positive locking.

8. The system for locking a dosing button according to claim 7 wherein said anti-rotation lock is formed by meshing engagement of ridges and furrows extending axially over a shell surface of said cylindrical dosing button, with ridges and furrows extending axially over a shell surface of said second indicator sleeve.

9. The system for locking a dosing button according to claim 7 wherein in said second position of said dosing button, said anti-rotation lock, between said dosing button and said second indicator sleeve, is released and said second indicator sleeve is rotatable relative to said first indicator sleeve.

10. The system for locking a dosing button according to claim 1 wherein between said housing and said second indicator sleeve a stop, acting in one direction of rotation of said second indicator sleeve, is formed to define a maximally selectable dose.

11. The system for locking a dosing button according to claim 1 wherein said device is used as an injection pen.

* * * * *

UNITED STATES PATENT AND TRADEMARK OFFICE
CERTIFICATE OF CORRECTION

PATENT NO. : 6,193,698 B1
DATED : February 27, 2001
INVENTOR(S) : Fritz Kirchhofer and Guido Hertig It is certified that error appears in the above-identified patent and that said Letters Patent is hereby corrected as shown below:

<u>Title page, item [54],</u>
The title reads "SYSTEM FOR LOCKING A DOSING BUTTON IN A DEVICE FOR THE ADMINISTRATION OF A PRODUCT TO BE INJECTED" should be -- SYSTEM FOR LOCKING A DOSING BUTTON IN A DEVICE FOR THE METERED ADMINISTRATION OF A PRODUCT TO BE INJECTED --

<u>Column 1,</u>
Line 32, reads "possible. In such" should be -- possible.
    In such --
Line 42, reads "complicated. It is" should be -- complicated.
    It is --

<u>Column 6,</u>
Line 35, reads "360E. This is" should be -- 360E.
    This is --
Line 37, reads "along the line A-A in accordance" should be -- along the line A-A in accordance --
Line 56, "un-shaped" should be -- u-shaped --

Signed and Sealed this

Sixteenth Day of October, 2001

*Attest:*

NICHOLAS P. GODICI
*Attesting Officer*     *Acting Director of the United States Patent and Trademark Office*